United States Patent [19]

Yoshida et al.

[11] Patent Number: 4,690,949
[45] Date of Patent: Sep. 1, 1987

[54] THERAPEUTIC DRUG FOR DEMENTIA

[75] Inventors: Mitsuo Yoshida; Yoshikuni Mizuno, both of Tochigi; Natsue Shimizu, Chiba; Mieko Otsuka; Masakatsu Dobutsu, both of Tochigi; Yuusuke Furukawa; Yutaka Joshita, both of Tochigi, all of Japan

[73] Assignee: Sumitomo Pharmaceuticals Company, Limited, Osaka, Japan

[21] Appl. No.: 857,239

[22] Filed: Apr. 29, 1986

[30] Foreign Application Priority Data

Oct. 31, 1985 [JP] Japan ................................ 60-245726

[51] Int. Cl.[4] .......................................... A61K 31/195
[52] U.S. Cl. ................................................... 514/561
[58] Field of Search ......................................... 514/561

[56] References Cited

U.S. PATENT DOCUMENTS 3,920,728 11/1975 Hegedus ............................. 514/567
4,330,558 5/1982 Suzuki ............................... 514/567
4,499,726 2/1985 Narabayashi ....................... 514/567
4,529,603 7/1985 Mori .................................. 514/567

OTHER PUBLICATIONS

Chem. Abst. 101-73099c (1984).
The Lancet "Selective Loss of Neurones of Origin . . . " Bondareff, Mountjoy, Roth Apr. 14, 1981, pp. 783-784.
Journal of Neurology, Neurosugery and Psychiatry, pp. 113-119, 1982, "The Noradrenergic System . . . " Mamann, et al.
British Medical Journal, vol. 282, pp. 93-94, "Reduced Dopamine-Beta-Hydroxylase . . . " Cross et al.

Primary Examiner—Stanley J. Friedman
Attorney, Agent, or Firm—Ladas & Parry

[57] ABSTRACT

A therapeutic drug for dementia is provided which comprises, as an active ingredient, DL- or L-threo-3,4-dihydroxyphenylserine of the formula

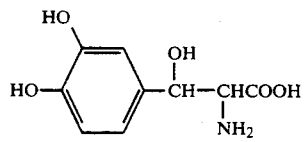

or its salt.

11 Claims, No Drawings

THERAPEUTIC DRUG FOR DEMENTIA

The present invention relates to a therapeutic drug for dementia which comprises, as an active ingredient, threo-3,4-dihydroxyphenylserine (hereinafter referred to as "Threo-DOPS"). The term "DOPS" used herein means a hydroxyamino acid of the formula(I)

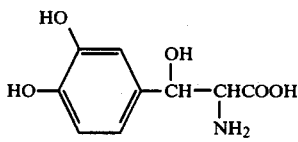

or its salt.

Recently, dementia is becoming a serious problem with the progress of the old age society. As symptomatological, neuropathological and etiological studies on dementia have become active, possibilities of the drug treatment for dementia have been looked for by various basic and clinical studies. So far, however, no drug has been found to be satisfactorily effective for dementia, and intensive studies have been conducted to find much more effective drugs for dementia.

The present inventors have been engaged in the drug treatment for dementia and now have found that Threo-DOPS improves conditions of patients with dementia.

It has been known that Threo-DOPS, which is a chemically synthesized amino acid, is decarboxylated by an action of an aromatic L-amino acid decarboxylase existing in the living body and converted into norepinephrine (NE); an important neurotransmitter of the central as well as sympathetic nervous systems.

More specifically, since Threo-DOPS is gradually converted to NE in the living body by administration orally or by injection, it may be considered to be a NE precursor which continuously and safely supplies NE.

Recently attentions have been paid to biochemical changes in the brain of patients with dementia. For instance, decrease of amino acids such as GABA, monoamines such as dopamine, serotonin and NE, acetylcholine (ACh) and peptides such as somatostatin, vasopressin and substance p has been reported. Although the contents of neurotransmitters or the related substances are reported to be generally decreased in the brain of the patient, it has not been sufficiently made clear as to which substance is specifically related to the basic brain functions such as memory or intelligence. There is, however, a story supported by a number of researchers that ACh is strongly related to memory.

It has been reported that some precursors of ACh such as choline or lecithin were administered to patients with dementia to replace decreased ACh and some effects were observed.

On the other hand, it has been reported that nerve cells of the Locus coeruleus of the brain of demented patients were decreased (W. Bondareff et al., 1982), that the content of NE in the brain was decreased (D. Mann et al., 1982) and that dopamine-$\beta$-hydroxylase, which is an enzyme for the biosynthesis of NE, was decreased in the frontal lobe, temporal lobe and hippocompus of the brain (A. J. Cross et al., 1981). These results support that NE is related to the intelligence which is composed of memory, calculation and orientation.

Based on the hypothesis that replacement of NE might have a therapeutic effect on demented patients, the present inventors examined whether Threo-DOPS might have beneficial effects on patients with dementia since the present inventors had alreadly experienced the effectiveness of Threo-DOPS as a NE precursor through clinical studies with Threo-DOPS on parkinsonian patients.

As a result, the present inventors have found that Threo-DOPS has an improving effect on some symptoms of dementia without any appreciable side effects, and thus have concluded that Threo-DOPS has clinical usefulness in the treatment of patients with dementia.

To evaluate the effectiveness of the drug for patients with dementia, however, it is important how to define or quantitate the symptoms of dementia. By quantitating various aspects of dementia or behavior of the demented patients, it seems possible to evaluate dementia objectively.

We have used following various tests: WAIS, Hasegawa's scale for intelligence, Osaka University tests for activity of daily life as well as mental functions, and records of psychological states. Furthermore, free association of letters and categories, paired memory test, Bourdon's test could safely be used to evaluate intelligence of demented patients, even with handicaps in hands or legs. We have done each test 4 times per patient at each point to evaluate the patient's mental state and thus this made us possible to get satisfactory statistical analysis.

Dementia could be classified into various clinical types according to the ethiology; such as Alzheimer's disease (AZ), senile dementia of Alzheimer type (SDAT), dementia due to the cerebral vascular diseases. We included these various types of dementia in this study.

Followings are detailed case reports.

(1) List of cases

List of cases with dementia and also evaluation of effectiveness of Threo-DOPS in each case are summarized in Table 1.

Administration schedule of L-Threo-DOPS and schedule of clinical evaluation are as follows:

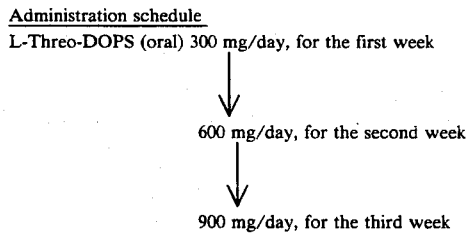

Administration schedule
L-Threo-DOPS (oral) 300 mg/day, for the first week
600 mg/day, for the second week
900 mg/day, for the third week Threo-DOPS were administered as follows; immediately after meals at 8:00, 12:00 and 17:00. Various psychological tests were performed at 10:00. The evaluations were performed on the day before and after administration of Threo-DOPS.

TABLE 1

| | List of Cases | | | | | | | | |
|---|---|---|---|---|---|---|---|---|---|
| Case No. | 1 | 2 | 3 | 4 | 5 | 6 | 7 | 8 | 9 |
| Age | 55 | 70 | 76 | 52 | 73 | 75 | 71 | 64 | 64 |
| Sex | Male | Male | Male | Male | Male | Male | Female | Female | Female |

TABLE 1-continued

| | | List of Cases | | | | | | | | |
|---|---|---|---|---|---|---|---|---|---|---|
| | Case No. | 1 | 2 | 3 | 4 | 5 | 6 | 7 | 8 | 9 |
| | Etiology | AZ | AZ | CI | CI | CI | AZ/CI | TH | TH | CI |
| Method of evaluation | Hasegawa | ND | ↓ | ↓ | ↑ | ↑ | → | ↑ | ↑ | ↑ |
| | N test | ND | ↑ | ↑ | ↑ | → | → | ↑ | ↑ | ↑ |
| | Bourdon's test | → | → | → | ↑** | ND | → | ND | ND | → |
| | Related words paired memory test | ↑*** | ↑*** | ND | → | ↑* | → | ND | ND | ↑** |
| | Digit symbol test | ↑* | ND | ND | ND | ND | ND | ND | ND | ND |
| Free association | Letter | ND | → | ND | → | → | → | ND | ND | → |
| | Category | ND | → | → | → | → | → | ND | ND | → |
| | $P_{300}$ | ND | + | − | + | − | − | + | + | − |

Abbreviation

Abbreviations used in the Table are as follows:
1. Etiology
   AZ: Alzheimer's disease
   CI: cerebral infarction
   TH: thalamic hemorrhage
2. Evaluation
   ND: The test not performed
   ↑: improved;
   ↓: aggravated;
   →: unchanged;
   +: appeared; −: disappeared
3. Statistics
   ***: $P<0.01$
   **: $P<0.02$
   *: $P<0.05$ Methods of Evaluation Evaluations were made as described below or by the methods used commonly.
1. Hasegawa's scale:
   Hasegawa, K. et al.: Clinical Psychiatry 16, 965–969 (1974)
   An increase or decrease of 10 percent from the pretreatment baseline score was regarded as "improved" or "aggravated".
2. N test:
   Inoue, O.: Medical Journal of the Osaka University 26, 375–394 (1974)
3. Bourdon's delection test:
   Matsumoto K. and Samezima K: Introduction to Clinical Psychology Tests, Igaku Shuppan Sha (Tokyo), 1977, pp. 83–87
   In this test, the original method was modified by enlarging the chart to make it easier for patients to see and conducting 4 test runs starting at different lines to investigate how far the task could be done in 30 seconds.
4. Paired memory test:
   This retention test using 10 pairs of related words was conducted in 4 trials and the results were compared before and after the treatment.
5. Digit symbol test:
   The original method of WAIS was partially modified. The test was repeated 4 times and counted time-in seconds which was required to finish one line or checked how far the subject could go along one line in 30 seconds.
6. Free association:
   Keye, W. H., Weingartier, H., et al.: Arzheimer's Disease, A Report of Progress, Aging 19, Raven Press (New York), 1982, pp. 433–442
   In this test, the subject was asked to say what would occur in mind by free association in response to the 4 letters of " " (a), " " (ka), " " (sa) and " " (ha) and the four categories of "fruits" or "vegetables", "flowers or trees", "animals" and "countries of the world" within 90 seconds and the number of words every 30 seconds was counted.
7. $P_{300}$:
   When two kinds of auditory stimuli are given randomly, a positive brain potential ($P_{300}$) appears with a latency of about 300 msec in normal subjects and this response has been considered to reflect gnostic function. [Sutton, S. et al.: Science 150, 1187–1188 (1965)].
   It is known that the latency of $P_{300}$ becomes longer with age and, in patients with dementia, shows a further prolongation or it disappears [Goodin, D. S. et al.: Brain 101, 635–648 (1978)].
   Using the method of Goodin, D. S. et al., the present inventors asked the subject to hear sounds of 1000 Hz and also 2000 Hz randomly given at intervals of about 1 second and to count the sounds of 2000 Hz which appeared 15% of the total number of sounds which were 400. The evoked potentials were averaged and totalled for each 1000 Hz and 2000 Hz stimulations and the latency and the amplitude of $P_{300}$ were measured.

Overall evaluation

As shown in Table 1, all subjects but Case 6 showed improvements in one or more tests. On the other hand, only a few evaluation parameters showed aggravation. It was, therefore, concluded that as a whole L-ThreoDOPS had efficacy against symptoms of patients with dementia.

No remarkable side effects were observed throughout the course of the clinical study. Based on these results, it was concluded that this compound has utility as a therapeutic drug for the patients with dementia.

(2) Referring to the above-mentioned list of cases, Cases 1, 7 and 9 will be explained in detail below.
   1. Case 1: Alzheimer's disease, age 55, male.

The patient's elder sister had an intellectual disturbance. Difficulty with daily conversation appeared in 1981 and the patient was examined in the department of neurology of a hospital in 1982 and diagnosed as having aphasia. Spontaneous speech was scanty and understanding of others' speech was impaired. In 1983 the symptoms were gradually aggravated and mistakes in daily work increased and, therefore, the patient was admitted to the department on Jan. 13, 1984 for detailed examination and treatment. Neurologically, there was disorientation of space and time but disturbance of memory as well as calculation was subtle. There was neither apraxia nor agnosia, and although spontaneous speech was possible, verbal understanding was severely impaired. Disturbance of motor as well as sensory function was unremarkable. Cerebral CT revealed marked cortical atrophy in the fronto-temporal lobe. Thus, in view of the cardinal manifestations of dementia and transcortical sensory aphasia with little change in personality, he was considered to have Arzheimer's disease. In this case, L-Threo-DOPS was administered in accordance with the schedule mentioned above.

Improvements were found in both "Related words paired memory test" and "digit symbol test". There were no remarkable side effects and the overall evaluation was "moderately improved".

2. Case 7: Left thalamic hemorrhage, age 71, female.

Her elder sister had cerebral infarction. Hypertension was pointed out 3 or 4 years ago and she was receiving antihypertensive drugs. On Aug. 15, 1984, at about 5 o'clock in the afternoon, a neighborer found the patient unconscious and squatting in the kitchen. Her consciousness recovered within an hour but could not stand and walk alone. At 8 p.m., nausea and vomiting appeared and consciousness began to be deteriorated again. She was hospitalized by emergency in the department on Aug. 16, 1984. On admission, neurologically the level of consciousness was somnolent and there were mild disorientation and memory disturbance. Calculation was impossible. Her right nasolabial fold was shallow. Muscle power of upper and lower limbs was less than 2/5 at right and less than 3/5 at left. Increased deep tendon reflexes of both upper limbs were found. Snout and sucking reflexes and bilateral Bakinski's sign were positive. Superficial sensation was low (8/10) at right side of the body. Cerebral CT performed on August 16 revealed hemorrhage extending from the left thalamus to the candate nucleus and perforated into the left ventricle. On Oct. 29, 1984, absorption of the hemorrhagic focus and the intraventricular hematoma was found by CT. While recitation was fairly well retained, utterance was scanty, and inertia, abulia and general slowness of intellectual activity were seen; she was in a state of thalamic dementia. L-Thero-DOPS was administered to her. Improvements were obtained in Hasegawa's scale, N mental function test, free association of things, and $P_{300}$, which could not be observed before the treatment, appeared after the treatment. No remarkable side effects were found. Globally, this case was judged as "markedly improved".

3. Case No. 9: Cerebral infarction, age 64, female.

The patient's father died of cerebral infarction. The patient had been taking drugs for hypertension for 10 years. Around 1984, tremor of hands and slowness of movements appeared. In January, 1985, Parkinson's disease was pointed out by a home doctor, and on April 12 of the same year, the patient was hospitalized in this department for detailed examination and treatment.

Neurologically disorientation was not remarkable, but slight memory disturbance and decreased calculation were found. Furthermore, constructive apraxia by examination of higher cerebral function was noted. In cranial nerve systems, the right nasolabial fold was shallow, and the right mouth angle was down. Concerning about motor functions, she showed stooped posture with the difficulty of first stepping. Increased deep tendon reflexes in both upper limbs, snout reflex and bilateral positive Babinski's sign were present. Cerebral CT revealed low-density areas in the watershed region, bilateral internal capsules and also bilateral putamens and the diagnoses of watershed infarction and infarctions of perforating arteries were made. She is in state of multi-infarct dementia. For treatment of the dementia associated with cerebral infarctions, L-Threo-DOPS was administered.

Improvements were found in Hasegawa's scale, N mental function test and related words paired memory test. No remarkable side effects were found. As a global evaluation, the case was judged as "moderately improved".

Threo-DOPS used in the present invention is capable of existing in the optical active L-form and D-form, as well as in the racemic DL-mixture. The clinical study by the present inventors confirmed that the L-isomer form is twice as active as the DL-form, and hence the L-isomer, administered in half the amount of the DL-mixture, produces nearly the same effect as the DL-mixture. In the present invention, Threo-DOPS therefore means either DL-Threo-DOPS or L-Threo-DOPS.

Threo-DOPS in the present invention can be prepared according to the methods disclosed in, for example, Japanese Published Patent Application (unexamined) Nos. 54-19931 and 56-29551.

Threo-DOPS may be used in the form of a pharmaceutically acceptable acid addition salt. In forming such a salt, any of inorganic acids such as hydrochloric acid, hydrobromic acid and sulfuric acid, and organic acids such as fumaric acid, citric acid, tartaric acid and succinic acid, may be used.

Threo-DOPS, the active ingredient of the present invention, may be administered orally or parenterally in an amount adequate to a particular need. More specifically, a therapeutic amount of the compound may orally be administered in a conventional preparation form such as tablets, capsules, syrups or suspensions. It may also be administered in the forms of, for example, solutions, emulsions or suspensions by injection.

These pharmaceutical preparations suitable for administration can be prepared by combining the active ingredient with acceptable conventional carriers, fillers, binding agents, stabilizers and the like. In the case where the active ingredient is used in the forms of injections, there may be added acceptable buffers, solubilizing agents, isotonizing agents and the like.

The dose of Threo-DOPS and the frequency of the administration vary depending upon the administration route and the degree of the disease. In case of the oral administration, the compound may be administered in an amount of 0.1-2 g, as the L-isomer, per adult patient per day at a single dosage or divided into several dosages.

In case of the intravenous injection, it may be administered in an amount of 0.025-0.5 g, as the L-isomer, per adult patient per day at a single dosage or divided into several dosages.

By the way, L-DOPA, which is now actually used as an anti-parkinsonian agent, is decarboxylated to the corresponding catecholamine, dopamine, by the action of a decarboxylase in the living body, just like Threo-DOPS.

Furthermore, L-DOPA is preferably used together with a peripheral decarboxylase inhibitor (hereinafter referred to as "DCI") since the blood L-DOPA level which is available for the brain, is markedly increased by suppressing the decarboxylation of L-DOPA in the peripheral tissue through the action of DCI.

The combined use of DCI has been known to reduce the amount of L-DOPA to be used as well as the side effects in the peripheral.

In case of Threo-DOPS, the combined use of DCI is not so effective as that for L-DOPA because, as has been revealed by the previous study of the present applicants, the rate of decarboxylation of Threo-DOPS is considerably smaller than that of L-DOPA. Accordingly, the combination of a small amount of DCI is enough to produce its effect, or DCI needs not be used at all.

In the present invention, a variety of DCI may be used. Preferred examples of DCI are Carbidopa and Benserazide. In combining DCI with Threo-DOPS for the above mentioned purpose, one tenth or less of the amount of Threo-DOPS is enough to produce the effect.

L-Threo-DOPS and DL-Threo-DOPS have very low toxicity. For example, $LD_{50}$ of the compound measured with mice was 10 g/Kg or more in case of oral administration and about 10 g/Kg in case of intraperitoneal injection. Thus, the compound can be considered to exert no harmful effect when administered at such dosages. Clinically, almost no side effect has been observed.

What is claimed is:

1. A method of treating dementia comprising administering to a patient suffering from dementia an effective amount of DL- or L-threo-3,4-dihydroxyphenylserine or a pharmaceutically acceptable salt thereof.

2. A method as in claim 1, wherein L-threo-3,4-dihydroxyphenylserine is administered.

3. A method as in claim 2, wherein said effective amount comprises 0.1–2 grams per day.

4. A method as in claim 3, wherein said compound is administered orally.

5. A method as in claim 1, wherein said effective amount comprises 0.025–0.5 grams per day.

6. A method as in claim 5, wherein L-threo-3,4-dihydroxyphenylserine is administered.

7. A method as in claim 6, wherein said L-threo-3,4-dihydroxyphenylserine is administered intravenously.

8. A method as in claim 1, wherein said dementia comprises Alzheimer's disease, or senile dementia of Alzheimer type.

9. A method as in claim 1 wherein said DL- or L-threo-3,4-dihydroxyphenylserine is administered in a tablet, capsule, syrup suspension, or emulsion.

10. A method as in claim 1 wherein the DL threo-3,4-dihydroxyphenylserine is administered in a composition comprising conventional carriers, fillers, binding agents, stabilizers, or buffers.

11. A method as in claim 3 wherein the DL threo-3,4-dihydroxyphenylserine is administered in a composition comprising conventional carriers, fillers, binding agents, stabilizers, or buffers.

* * * * *

UNITED STATES PATENT AND TRADEMARK OFFICE
CERTIFICATE OF CORRECTION

PATENT NO. : 4,690,949
DATED : September 1, 1987
INVENTOR(S) : Mitsuo Yoshida, et al It is certified that error appears in the above-identified patent and that said Letters Patent is hereby corrected as shown below:

Title page, assignee data,

Add the following assignee:

YOSHIDA, Mitsuo
Tochigi, Japan

Signed and Sealed this

Sixth Day of September, 1988

Attest:

DONALD J. QUIGG

Attesting Officer

Commissioner of Patents and Trademarks